United States Patent
Pinchuk et al.

(10) Patent No.: US 10,219,943 B2
(45) Date of Patent: Mar. 5, 2019

(54) GLAUCOMA DEVICE DELIVERY SYSTEM AND TRANS-CONJUNCTIVAL METHOD OF DELIVERY

(71) Applicant: InnFocus, Inc., Miami, FL (US)

(72) Inventors: Leonard Pinchuk, Miami, FL (US); John B. Martin, Miami, FL (US); Anh Le, Miami Lakes, FL (US)

(73) Assignee: InnFocus, Inc., Miami, FL (US)

(*) Notice: Subject to any disclaimer, the term of this patent is extended or adjusted under 35 U.S.C. 154(b) by 348 days.

(21) Appl. No.: 15/192,291

(22) Filed: Jun. 24, 2016

(65) Prior Publication Data

US 2016/0374856 A1    Dec. 29, 2016

Related U.S. Application Data

(60) Provisional application No. 62/185,347, filed on Jun. 26, 2015, provisional application No. 62/263,786, filed on Dec. 7, 2015.

(51) Int. Cl.
*A61F 9/007* (2006.01)
*A61B 17/34* (2006.01)

(52) U.S. Cl.
CPC ...... *A61F 9/00781* (2013.01); *A61B 17/3415* (2013.01)

(58) Field of Classification Search
CPC ... A61B 17/3415; A61F 9/00781; A61F 9/007
See application file for complete search history.

(56) References Cited

U.S. PATENT DOCUMENTS 6,589,203 B1   7/2003   Mitrev
7,431,709 B2   10/2008  Pinchuk et al.
(Continued)

FOREIGN PATENT DOCUMENTS

WO    WO 2011/106781 A1    9/2011
WO    WO 2013/158919 A1    10/2013

*Primary Examiner* — Leslie Deak
(74) *Attorney, Agent, or Firm* — Gordon & Jacobson, P.C.

(57) ABSTRACT

A method for treating glaucoma with an implantable glaucoma device includes inserting a hollow elongated needle into the eye between the cornea and iris and into the anterior chamber of the eye to form a needle tract in the eye, introducing a distal end of a guidewire through the needle and into the anterior chamber, introducing a snare through a corneal incision into the anterior chamber. The snare has a sheath and a hook or loop inside the sheath and extendible therefrom. The method includes capturing a segment of the guidewire proximate the distal end of the guidewire with the snare within the anterior chamber, removing the needle from over the guidewire outside of the eye, coupling a glaucoma drainage device to a proximal end of the guidewire that extends outside of the eye, and pulling on the captured guidewire segment with the snare to pull the glaucoma drainage device into the needle tract and into the anterior chamber of the eye until the glaucoma device is located in an implanted position in the eye. The method can also possibly involve removing the snare from the eye, cutting a distal end of the glaucoma device (possibly within the anterior chamber), and removing the cut distal end of the glaucoma drainage device from the eye. An improved glaucoma drainage device and other deployment systems and methods are also described and claimed.

12 Claims, 14 Drawing Sheets

(56) References Cited

U.S. PATENT DOCUMENTS

| | | |
|---|---|---|
| 7,594,899 B2 | 9/2009 | Pinchuk et al. |
| 7,837,644 B2 | 11/2010 | Pinchuk et al. |
| 8,672,870 B2 | 3/2014 | Silvestrini et al. |
| 8,734,378 B2 | 5/2014 | De Juan, Jr. et al. |
| 9,101,444 B2 | 8/2015 | Pinchuk |

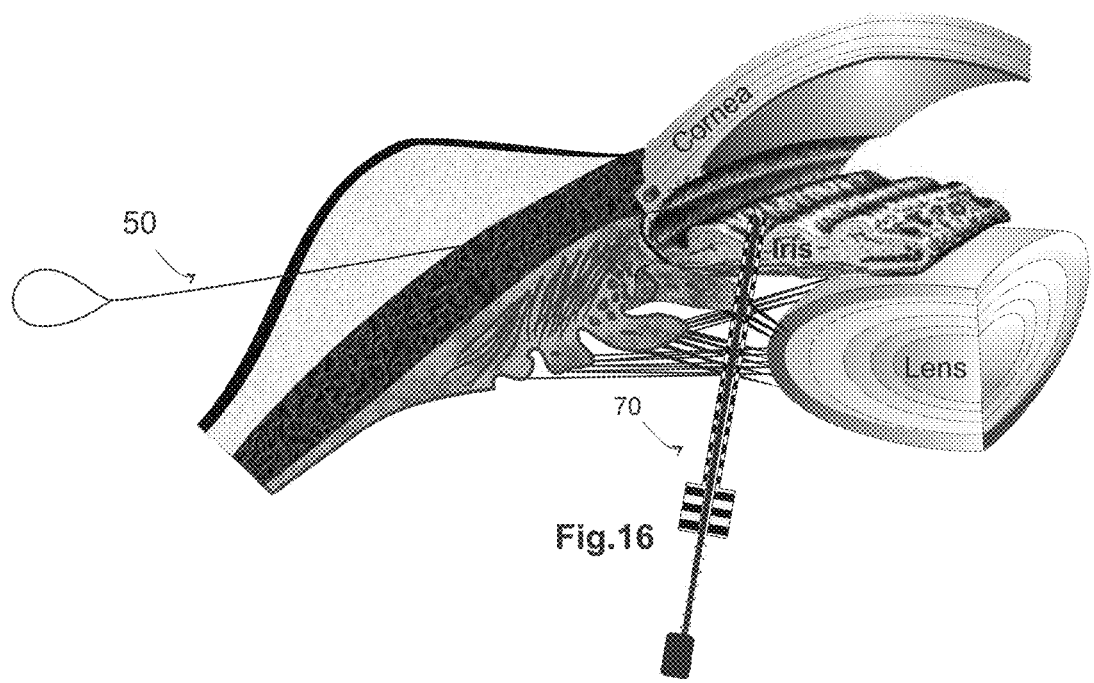
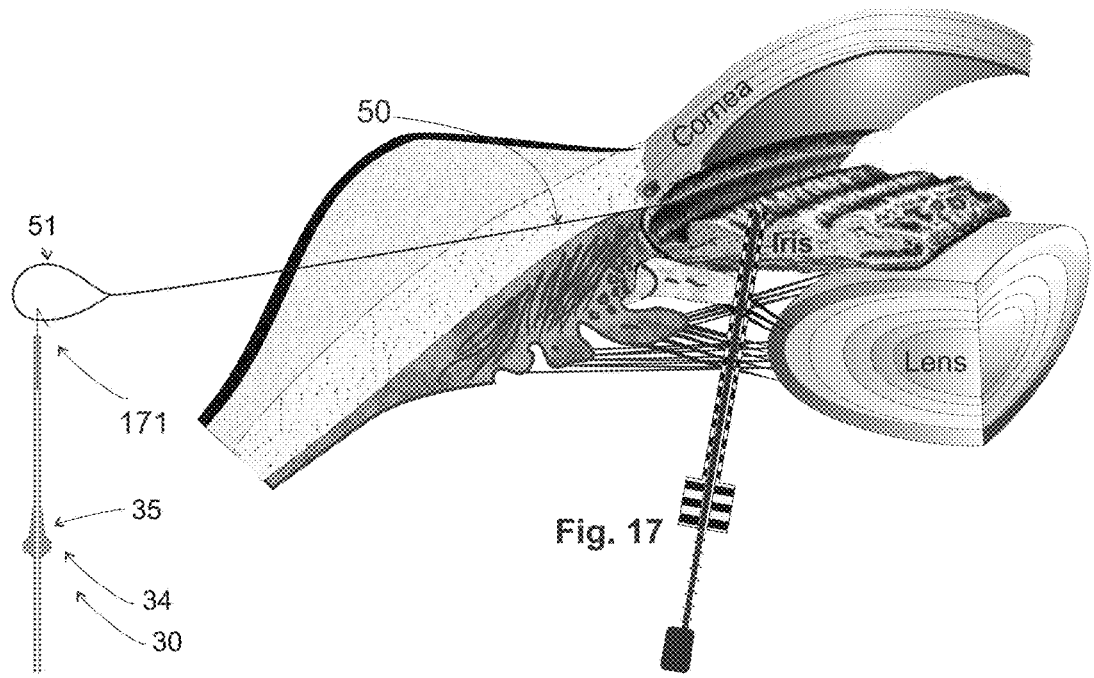

GLAUCOMA DEVICE DELIVERY SYSTEM AND TRANS-CONJUNCTIVAL METHOD OF DELIVERY

CROSS-REFERENCE TO RELATED PATENTS AND APPLICATIONS

This application claims priority from U.S. Provisional Application Nos. 62/185,347, filed on Jun. 26, 2015, and 62/263,786, filed on Dec. 7, 2015, which are hereby incorporated by reference herein in their entireties.

BACKGROUND

1. Field

The disclosure relates to eye surgery. More particularly, the disclosure relates to systems and methods for treating glaucoma with a glaucoma drainage device.

2. State of the Art

Co-owned U.S. Pat. Nos. 7,431,709, 7,594,899 and 7,837,644 and U.S. Publication No. 2013/0184631A1 describe an elongate glaucoma drainage device (or shunt) as generally shown in Prior Art FIG. 1, which includes a tube 2 with a lumen 3, a fin 4, a beveled distal tip 5, and a proximal end 6. The lumen 3 extends between the distal tip 5 and the proximal end 6 of the tube 2. The glaucoma drainage device 1 may be coated or impregnated with an antiproliferative drug such as Mitomycin C or 5-Fluoro Uracil.

Referring to Prior Art FIG. 2, the current procedure for inserting the glaucoma drainage device 1 of Prior Art FIG. 1 into the eye (referred to herein as "glaucoma implant surgery") includes the following steps: 1) anesthetizing the eye by injecting lidocaine and epinephrine under the conjunctiva; 2) incising below the limbus and dissecting a flap posterior with a blunt-tipped scissors; 3) placing three LASIK shields saturated with Mitomycin C (0.2 to 0.4 mg/ml) in the flap for 3 minutes followed by irrigation with saline; 4) forming a radial, shallow scleral pocket, approximately 1 mm wide×1 mm in length into the sclera with a sharp knife; 5) inserting a 25 or 27 gauge needle through the apex of the scleral pocket into the anterior chamber wherein the course of the needle approximately bisects the angle formed between the iris and cornea; 6) threading the glaucoma drainage device 1 through the needle tract with a forceps until the distal end of the device (the end furthest away from the surgeon) enters the anterior chamber of the eye; 7) wedging the fin 4 of the glaucoma drainage device snugly into the scleral pocket; and 8) pulling the conjunctiva and Tenon's capsule over the proximal end 6 of the glaucoma drainage device 1 and suturing the flap closed. The entire procedure typically takes 15 to 25 minutes to perform. After the glaucoma implant surgery, the lumen 3 of the glaucoma drainage device 1 provides a flow path for the drainage of aqueous humor from the anterior chamber of the eye into the scleral pocket in order to control TOP of the eye. The pressure drop between the anterior chamber of the eye and the scleral pocket is dictated primarily the interior diameter of the lumen 3 of the glaucoma drainage device 1. Thus, the interior diameter of the lumen 3 can be varied amongst patients for control of TOP for different patients.

Although the aforementioned glaucoma drainage device and the glaucoma implant surgery function well, there is a need to simplify and expedite the procedure. Interviews with many cataract surgeons have indicated that they will perform the glaucoma implant surgery at the time of cataract surgery if there is no conjunctival dissection, no bleeding, no suturing and if the procedure is reduced to less than 5 minutes. Cataract surgeons treat approximately 3 million eyes per year in the U.S. and approximately 20% of patients have glaucoma. This represents a potential market of 600,000 cases per year, which is sufficiently substantial to satiate cataract surgeons with a glaucoma implant surgical procedure better suited to their requirements.

It is important to know that when cataract surgery is performed, two clear corneal incisions are made in the cornea to allow instrumentation to be inserted into the eye to remove the cataractous lens and subsequently replace the lens with an intraocular lens. Further, the anterior chamber is enlarged with a viscous fluid to enable performing the cataract procedure without damaging the endothelial cells under the cornea. The viscous fluid does not leak through the clear corneal incisions.

SUMMARY

Systems and procedures are provided that enable implanting an elongate glaucoma drainage device in a relatively simple and reproducible manner. The procedures can be performed in combination with cataract surgery or on its own. If performed on its own, at least one incision must be made in the cornea. The use of a viscous fluid in the anterior chamber is optional.

In embodiment(s), the instruments used in the method include a syringe, a needle, a guidewire, and a snare, all for implanting the glaucoma drainage device. Some or all of the instruments may be provided as a kit, with or without the glaucoma drainage device. The guidewire and snare can be provided in a kit, as they are used together to implant the glaucoma drainage device. The method includes the following steps. A syringe is inserted into Tenon's capsule, and a fluid is injected from the syringe into Tenon's capsule to expand Tenon's capsule. The needle is then inserted between the cornea and the iris to form a first tissue passageway (or needle tract) leading into the anterior chamber of the eye. The guidewire is inserted through the needle and into the anterior chamber. A snare is then inserted through a corneal incision that forms a second tissue passageway leading into the anterior chamber of the eye. The snare engages the end of the guidewire within the anterior chamber. The needle is then removed from over the guidewire. The distal end of the elongate glaucoma drainage device is then coupled to an end of the guidewire that extends outside of the eye. The guidewire is then operated to pull the glaucoma drainage device (distal end first) into the needle tract until the glaucoma drainage device is located in the desired position in the eye (with the distal end inside the anterior chamber of the eye). The distal end of the glaucoma drainage device can then cut to length within the anterior chamber, if desired, and the unnecessary cut length and snare can be retracted from the eye through the second tissue passageway.

In embodiment(s), a delivery device for an elongate glaucoma drainage device includes a guidewire with a hollow cap and retainer member secured to the guidewire at fixed positions offset from one another along the length of the guidewire. The cap is configured to receive and carry one end (e.g., the distal tip 5) of an elongate glaucoma drainage device. In this configuration, the one end of the glaucoma drainage device is disposed and carried within the interior space of the hollow cap without the one end of the glaucoma drainage device being affixed to the cap. The retaining member is spaced longitudinally from the cap to accommodate the length of the glaucoma drainage device and prohibit the glaucoma drainage device from sliding out of the interior space of the opposed cap during use. The guide wire, cap and retainer member can be configured to capture and carry the glaucoma drainage device during deployment through ocular tissue. An elongate glaucoma drainage device can be packaged with the delivery device to provide an assembly for delivering the glaucoma drainage device.

In embodiment(s), the guidewire of the delivery device (or assembly) can be configured to slide through the lumen of the glaucoma drainage device such that guide wire, cap and retainer member capture and carry the glaucoma drainage device as the distal end of the glaucoma drainage device is pulled through a tissue tract leading to the anterior chamber of the eye such that the glaucoma drainage device is implanted at a desired location (for example, where the cap and the distal end of the glaucoma drainage device are positioned inside the anterior chamber of the eye). The retaining member can be detached from the guide wire, which allows the cap and the guide wire to be separated from the glaucoma drainage device by further pulling of the guide wire. Because the retaining member is detached from the guide wire, the further pulling of the guide wire does not move the glaucoma device form its implanted position. The cap and guidewire can be pulled and withdrawn through the incision leading into eye such that the cap and guidewire are removed from the eye. The proximal end of the glaucoma drainage device can be located in space that allows for drainage of aqueous humor from the anterior chamber of the eye through the lumen into such space.

In another aspect, a glaucoma drainage device is provided for implantation in an eye, which includes a tube having a distal end and a proximal end. An internal lumen extends within the tube between the distal and proximal ends of the tube. An external fixation means extends radially outward from the tube intermediate the distal and proximal ends of the tube. The fixation means includes a taper and a shoulder. The taper extends along a portion of the length of the tube between a taper distal end and taper proximal end. The taper has a larger diameter at the taper proximal end than at the taper distal end. The shoulder has a bearing surface that extends from the taper proximal end. The device is positionable in a needle tract formed in tissue with a needle having an outer diameter, the shoulder having an outer diameter at least twice the outer diameter of the needle. The taper distal end can have a diameter that is sized approximately the same as the outer diameter of the tube and less than the outer diameter of the needle, and the taper proximal end can have a diameter that is greater than the outer diameter of the needle. The taper can be positioned within the eye to engage and seal ocular tissue of a tissue passageway through which the distal end of the tube is inserted. The bearing surface of the shoulder can be positioned within the eye to bear against the ocular tissue at the proximal end of the tissue passageway to prevent further movement of the device into the tissue passageway.

BRIEF DESCRIPTION OF THE DRAWINGS

Prior Art

Prior Art

FIG. 16 is a view similar to FIG. 15 showing the needle removed from over the guidewire.

FIG. 17 is a view similar to FIG. 16 showing attachment of a glaucoma drainage device to an end of the guidewire.

DETAILED DESCRIPTION OF THE PREFERRED EMBODIMENTS

The invention provides devices and methods to enable implanting the glaucoma device in a relatively simple, quick, and reproducible manner. The procedure can be performed in conjunction with cataract surgery or separately on its own. If performed on its own, at least one incision must be made in the cornea. The use of a viscous fluid in the anterior chamber is optional.

Figure 1:
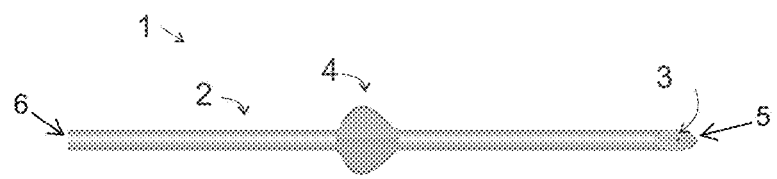
FIG. 1 is a side elevation of a prior art glaucoma drainage device.
Figure 2:
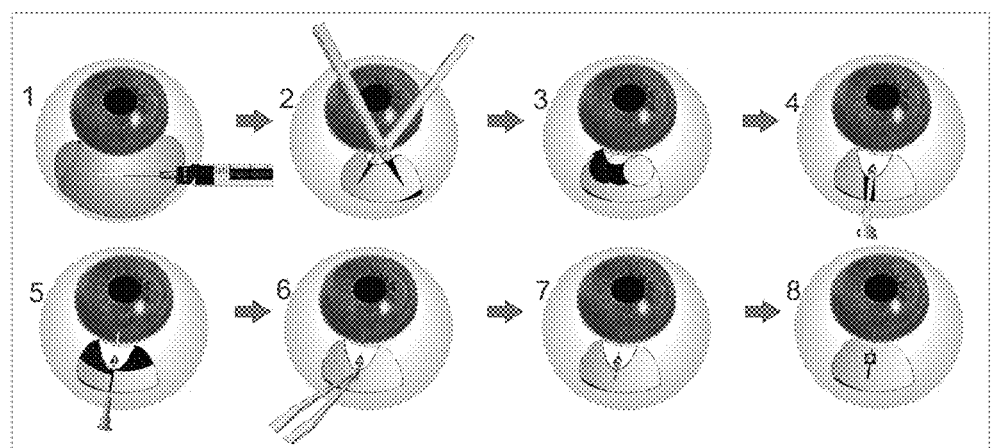
FIG. 2 illustrates the series of steps in a prior art procedure for implanting the glaucoma drainage device of Prior Art FIG. 1 into the eye.
Figure 3:
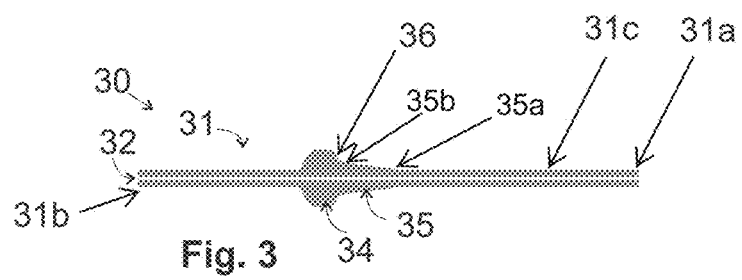
FIG. 3 is a side elevation of a glaucoma drainage device.

Turning now to FIG. 3, an elongate glaucoma drainage device 30 is shown that differs from the device 1 shown in Prior Art FIG. 1. Glaucoma drainage device 30 is comprised of tube 31 with a distal end 31a opposite a proximal end 31b. A lumen 32 extends between the distal end 31a and the proximal end 31b. Fixation means 33 is disposed intermediate the distal end 31a and the proximal end 31b. The fixation means 33 extends radially outward with respect to the outer surface 31c of the tube 31. The fixation means 33 includes a shoulder 34 and a taper 35. The taper 35 forms a seal to the ocular tissue along a lengthwise section of a needle tract 37 (FIG. 4B) to prevent ocular fluid from leaking from the anterior chamber 42 (FIG. 4A) of the eye and around the tube 31 when the glaucoma drainage device 30 is implanted into the eye as described below with respect to FIGS. 4A and 4B. The shoulder 34 is a projection or abrupt change in shape or diameter designed to withstand thrust forces. The shoulder 34 includes a bearing surface 36 that acts as a transition from the taper 35. The bearing surface 36 can also bear against and contact ocular tissue at the proximal end of the needle tract 37 into which the glaucoma drainage device 30 is implanted, wherein the bearing surface 36 withstands thrust forces in the direction away from the proximal end 31b toward the distal end 31a of the glaucoma drainage device 30. For example, such thrust forces can be produced by eye movement (such as blinking) when the glaucoma drainage device 30 is implanted into the eye. In this manner, the bearing surface 36 of the shoulder 34 can prevent movement and migration of the glaucoma drainage device 30 through the needle tract 37 toward and possibly into the anterior chamber of the eye.

Note that FIG. 3 is a section view that shows the outer profile of the glaucoma drainage device 30. The three-dimensional structure of the glaucoma drainage device 30 can be defined by revolving the outer profile surfaces of the glaucoma drainage device 30 about an axis through the lumen 32. In one embodiment, the outer surface 31c of the tube 31 has a diameter of about 0.35 mm and the lumen 32 of the tube 31 has a diameter of about 50 to 100 microns, and preferably about 70 microns. The taper 35 has a distal end 35a that may have the same diameter as the outer diameter of the tube, i.e., 0.35 mm. Also, the taper 35 has a proximal end 35b that has an outer diameter that may be about 0.40 to 0.60 mm. The length of the taper 35 may be about 1.5 mm to 2.0 mm. The bearing surface 36 provides an abrupt transition between the proximal end 35b of the taper 35 and the widest portion 34a of the shoulder 34. The profile of the bearing surface 36 may be curved as shown in FIG. 3 or possibly a linear step. Also, while the profile of the taper 35 is shown as being generally linear (e.g., conical or frusto-conical), it may also be partially linear, or partially or fully curved (e.g., concave or convex).

Figure 4A:
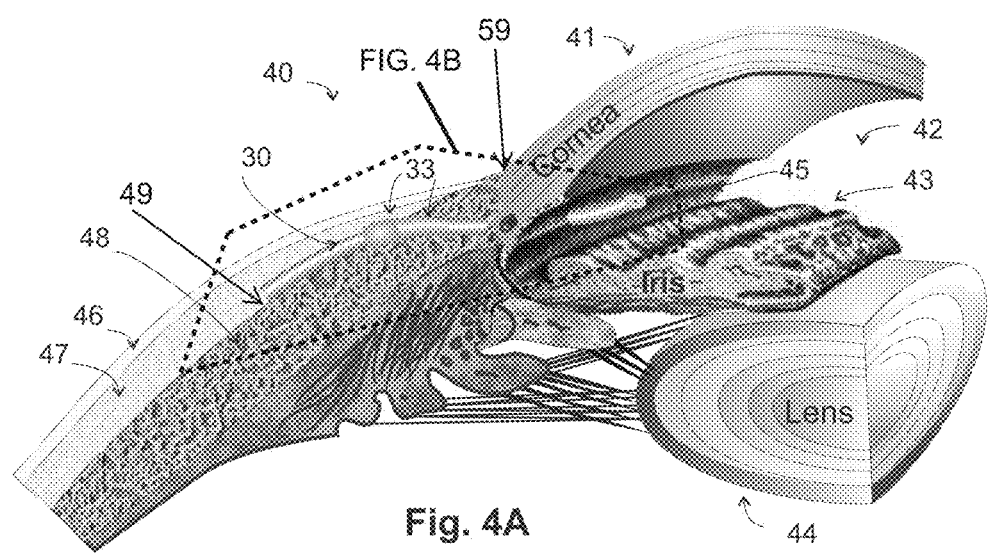
FIG. 4A is a sagittal view of the glaucoma drainage device of FIG. 3 implanted in the eye.

As will be discussed later, the taper 35 is inserted into the needle tract 37 (FIG. 4B) formed through the conjunctiva 46 (FIG. 4A), Tenon's capsule 47 (FIG. 4A), and sclera 48 (FIG. 4A). The taper 35 contacts to the surrounding ocular tissue of the needle tract 37 to form a seal to such ocular tissue along a lengthwise section of the needle tract 37 to prevent ocular fluid from leaking from the anterior chamber 42 (FIG. 4A) of the eye and around the glaucoma drainage device 30. If effect, the taper 35 acts as a stopper to prevent fluid from leaking around the glaucoma drainage device 30. In the embodiment shown in FIG. 3, the diameter of the shoulder 34 at the widest portion 34a (i.e., the maximal dimension of the shoulder 34) may be at least twice the diameter of a needle 120 (FIG. 12) used to form the needle tract 37 as described herein below. In one example, where the needle 120 has an outer diameter of 0.51 mm (25 gauge needle), the maximal dimension of the shoulder 34 is about 0.09 mm to 1.2 mm, or at least twice the outer diameter of the needle 120.

As will be discussed later, when implanted, the shoulder 34 of the fixation means 33 remains outside the proximal end of needle tract 37 (FIG. 4B) and the bearing surface 36 of the shoulder 34 can bear against and contact ocular tissue at the proximal end of the needle tract 37 into which the glaucoma drainage device 30 is implanted. In this configuration, the bearing surface 36 withstands thrust forces in the direction away from the proximal end 31b toward the distal end 31a of the glaucoma drainage device 30. For example, such thrust forces can be produced by eye movement (such as blinking) when the glaucoma drainage device 30 is implanted into the eye. In this manner, the bearing surface 36 of the shoulder 34 can prevent movement (migration) of the glaucoma drainage device 30 through the needle tract 37 toward and possibly into the anterior chamber of the eye.

In one embodiment, the materials comprising the glaucoma drainage device 30 are the same materials as described in U.S. Pat. Nos. 7,431,709, 7,594,899 and 7,837,644, commonly assigned to assignee of the present invention and herein incorporated by reference in their entireties. Although FIG. 3 shows a slightly different version of the drainage device 1 shown in Prior Art FIG. 1, both designs can be used with the systems and methods as described herein.

FIG. 4A illustrates a sagittal view of the eye 20 with cornea 41, anterior chamber 42, iris 43, lens 44, conjunctiva 46, Tenon's Capsule (also called the Tenon's membrane) 47, sclera 48, and a space (termed a "bleb") 49 formed between Tenon's Capsule 47 and sclera 48. The anterior chamber 42, which is the space between the iris 43 and the cornea 41, contains a clear fluid called aqueous humor, which is essential for the proper functioning of the eye. The aqueous humor, which is made at a fairly constant rate, passes around the lens 44, through the pupil in the iris 43 and into the anterior chamber 42. The aqueous humor naturally drains out of the anterior chamber 42 either through the conventional channel or through the uveoscleral channel.

Figure 4B:
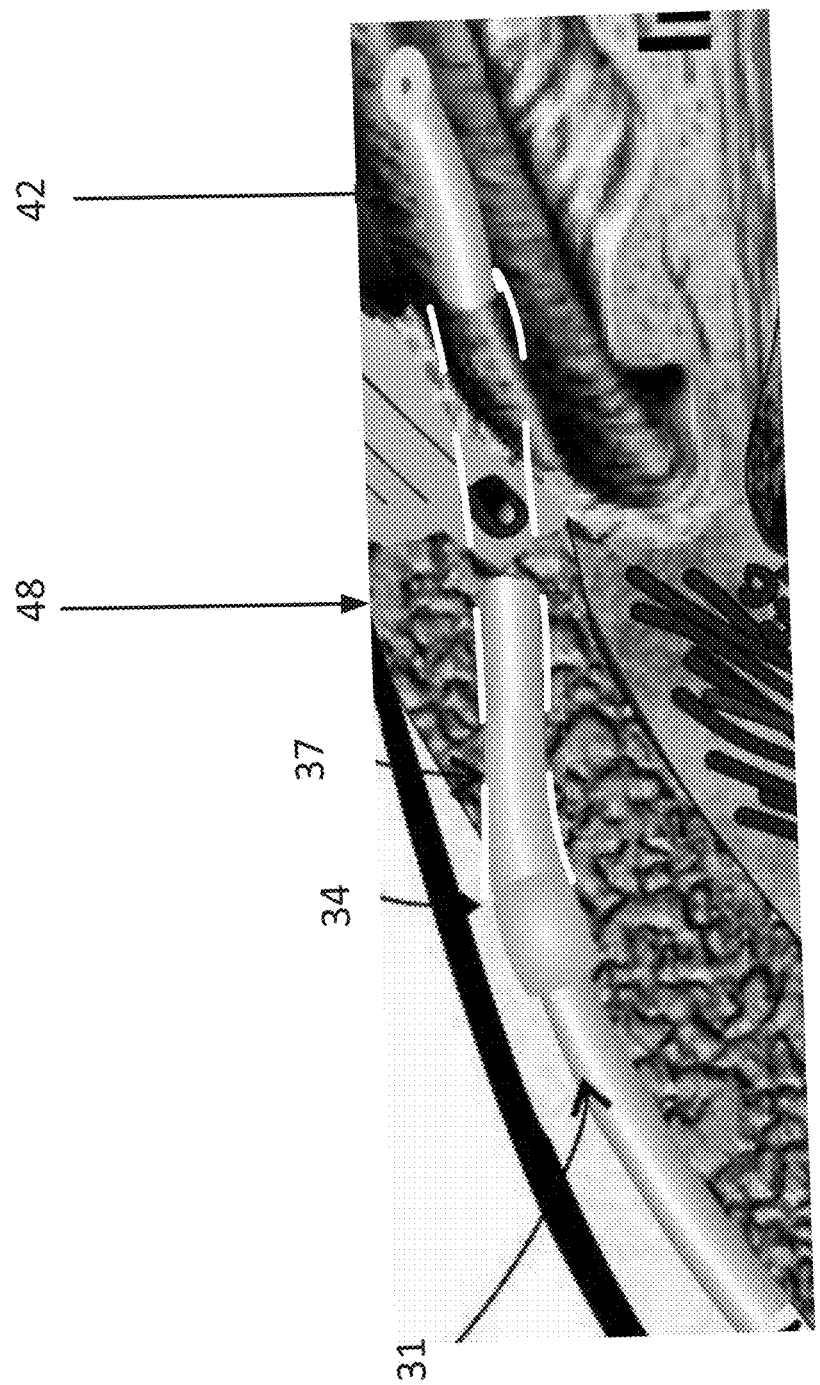
FIG. 4B is an exploded view of area 4B in FIG. 4A.

FIGS. 4A and 4B show the glaucoma drainage device 30 in an implanted position in the needle tract 37. The depiction of the eye 40 includes the cornea 41, anterior chamber 42, iris 43, lens 44, trabecular meshwork 45, conjunctiva 46, Tenon's capsule 47, and sclera 48. Note that the shoulder 34 of the glaucoma drainage device 30 remains slightly outside the sclera 48 adjacent the proximal end of the needle tract 37 and the taper 35 of the glaucoma drainage device 30 is wedged into the needle tract 37 formed in the sclera 48 as best shown in FIG. 4B where the needle tract 37 is outlined by a dashed white line. The bearing surface 36 of the shoulder 34 may contact or bear against the sclera 48 to withstand thrust forces in the direction away from the proximal end 31b toward the distal end 31a of the glaucoma drainage device 30. For example, such thrust forces can be produced by eye movement (such as blinking) when the glaucoma drainage device 30 is implanted into the eye. In this manner, the bearing surface 36 of the shoulder 34 prevents movement and migration of the glaucoma drainage device 30 through the needle tract 37 toward and possibly into the anterior chamber of the eye. The taper 35 contacts to the surrounding sclera 48 of the needle tract 37 to form a seal to such ocular tissue along a lengthwise section of the needle tract 37 to prevent ocular fluid from leaking from the anterior chamber 42 (FIG. 4A) of the eye and around the glaucoma drainage device 30. If effect, the taper 35 acts as a stopper to prevent fluid from leaking around the glaucoma drainage device 30.

Figure 5:
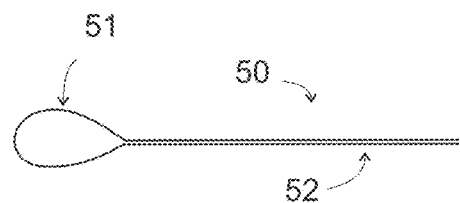
FIG. 5 is a side elevation schematic of one embodiment of a guidewire used in a procedure described herein.
Figure 6:
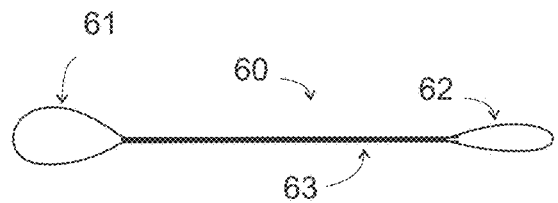
FIG. 6 is a side elevation schematic of another embodiment of a guidewire used in a procedure described herein.
Figure 12:
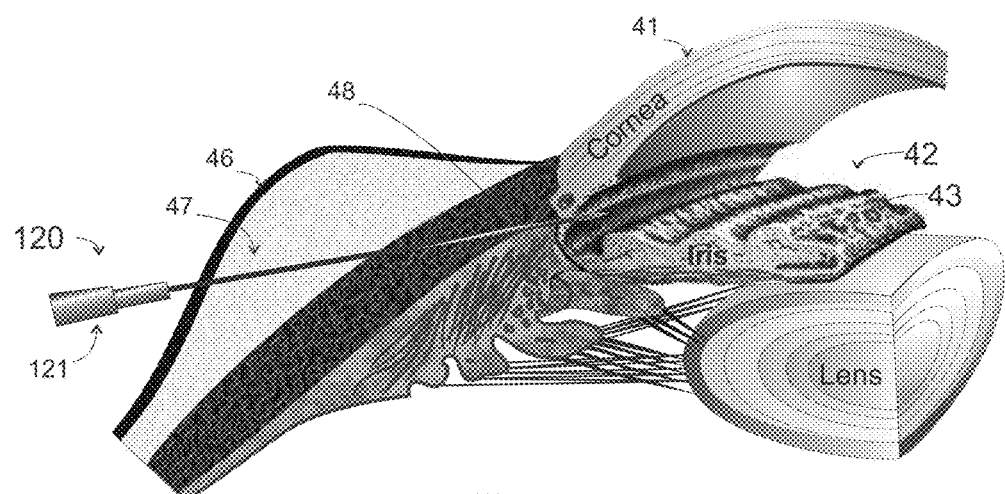
FIG. 12 is a view similar to FIG. 10 showing insertion of a needle between the cornea and iris and into the anterior chamber of the eye.

The remaining figures show the instrumentation and methodology used to implant the glaucoma drainage device 30 (or device 1) into the eye 40. FIG. 5 shows a guidewire 50 with a loop 51 and wire 52. FIG. 6 shows an alternative guidewire 60 with loops 61 and 62 on both ends of wire 63. Guidewires 50 and 60 are both made by twisting or soldering respective wires 52 and 63 together while maintaining the respective loop sections 51 and 61/62 open. The twisted wires 52 of guidewire 50 and the twisted wires 63 of guidewire 60 may also be soldered together. The guidewires 50, 60 are made from medical grade wire such as stainless steel, Elgiloy®, nitinol, titanium, and the like, and are rust resistant. It is preferred that the guidewires 50 and 60 have some elasticity such that the respective loops 51 and 61/62 open when removed from a compressed state. Wire diameters of the wires 52 and 63 are generally 0.001 inches to 0.006 inches; preferable 0.0020 inches to 0.0040 inches; and most preferably 0.0025 inches. When paired and twisted, the guidewires 50 and 60 can fit inside a delivery needle (e.g., needle 120 (FIG. 12). In embodiment(s), the delivery needle may be a 25 gauge needle having a lumen (or inner diameter) of 0.008 inches.

Figure 7A:
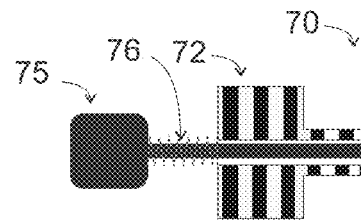
FIGS. 7A and 7B illustrates a snare device and operation thereof between extended and retracted positions.
Figure 7B:
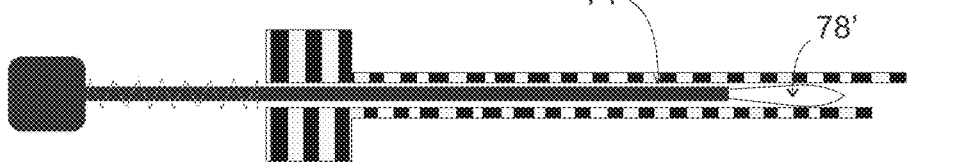

FIGS. 7A and 7B show a snare 70 that may be used to snare the non-looped end of guidewire 50. Snare 70 includes an outer cylinder or sheath 71 that is connected to a proximal grip 72 at a proximal end. Opposite to grip 72 is a distal end 73, which can be beveled, or even pointed, to facilitate entry of the distal end 73 into and through the cornea 41, even without a prior incision in the cornea 41. An inner tube 74 is slidable within the outer tube 71. The inner tube 74 is connected to a proximal knob 75. Resting between grip 72 and knob 75 is a spring 76 that forces the knob 75 away from the grip 72. The inner tube 74 has a distal end 77 that is connected to a wire loop 78.

Figure 8:
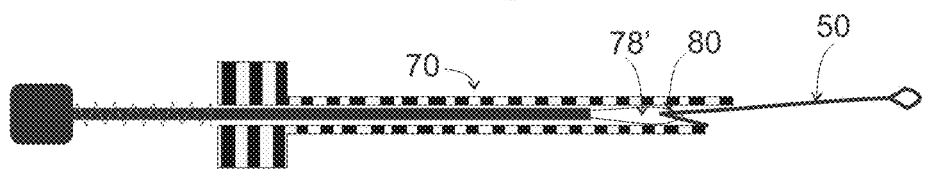
FIG. 8 illustrates use of the snare device to snare an end of the guidewire.

The function of the snare 70 is as follows. As shown in FIG. 7A, when the knob 75 is displaced towards the grip 72, the spring 76 is compressed and the loop 78 extends out of the outer sheath 71. When the knob 75 and spring 76 are relaxed, as shown in FIG. 7B, the spring 76 expands, thereby retracting the inner tube 74 and the loop 78 into the outer sheath 71. Although not shown in FIGS. 7A or 7B, the snare 70 may include structures to reinforce the inner tube 74, as well as structures to prevent the inner tube 74 from separating from the outer sheath 71. As shown in FIG. 8, when the wire 52 of guidewire 50 is inserted into the loop 78 of snare 70, and the knob 75 and spring 76 are relaxed, the wire 52 will be snared or captured by the loop 78. By providing the spring 76 with sufficient strength, and the wire 52 with sufficient malleability, the non-looped end of the wire 52 can be bent onto itself and brought into outer sheath 71 of the snare 70, as shown in FIG. 8. For example, in the example shown in FIG. 8 the guidewire 50 is forced to bend at point 80 and retract into the outer sheath 71. This feature is important in that capturing the end of guidewire 50 can prevent the end of guidewire 50 from damaging endothelial cells under the cornea 41. The materials comprising the snare 70 may generally include stainless steel hypodermic tubing and wire. The grip 72 and the knob 75 may be made from plastic (acrylic, polycarbonate, ABS, etc.).

Although FIGS. 7A, 7B, and 8 show a spring-containing device, it will be appreciated that a similar snare actuator (not shown) can be made where the knob 75 is replaced with a hand-held handle and the grip 72 is replaced with a thumb slide to effectuate the same relative motion of the loop 78 relative to the outer sheath 71 by motion of the thumb slide relative to the handle.

Figure 9:
FIG. 9 illustrates an alternate embodiment of a snare device.

FIG. 9 shows an alternate embodiment of the snare 70 that includes a hooked rod 90 with a shaft 91 and hook 92, which may be used to hook the loop 62 of guidewire 60 shown in FIG. 6. The combination of guidewire 50 and snare 70 is preferred as there is less chance of a sharp wire damaging the corneal endothelial cells. The combination of guidewire 50 and snare 70 will be used to demonstrate the implant procedure hereafter; however, the combination of hooked rod 90 can just as easily be used with guidewire 60.

Figure 10:
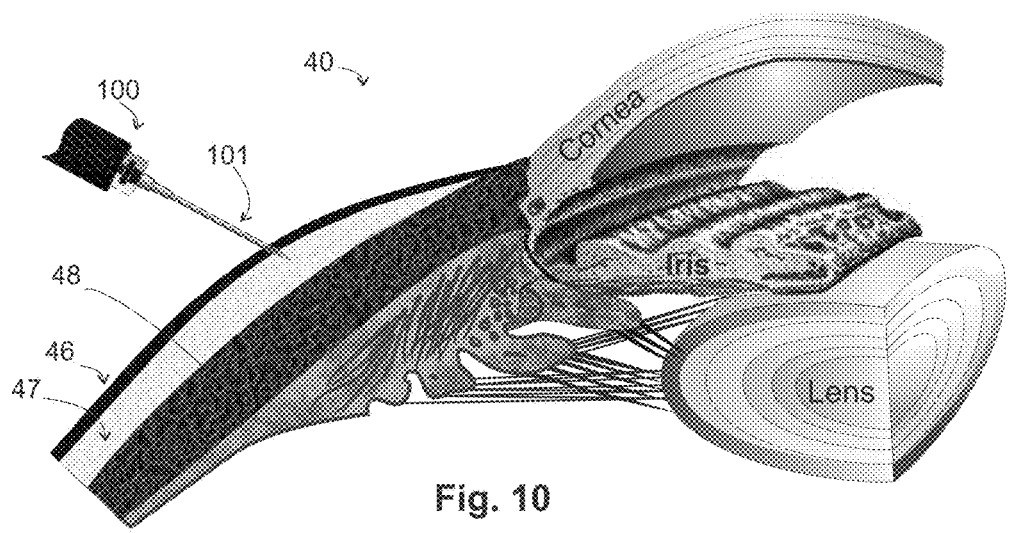
FIG. 10 is a sagittal view of the eye and illustrates insertion of a syringe into Tenon's capsule according to a method described herein.
Figure 11:
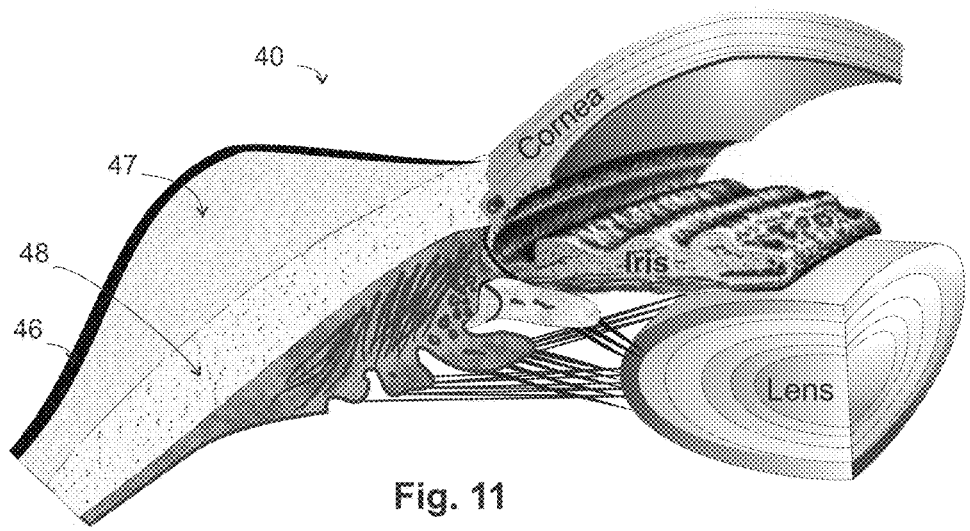
FIG. 11 is a view similar to FIG. 10 showing expansion of Tenon's capsule with fluid from the syringe.

In embodiment(s), the glaucoma drainage device 30 can be implanted in the eye 40 in the manner described below with respect to FIGS. 10 to 20. As shown in FIG. 10, a syringe 100 is charged with medicinal combinations which can include lidocaine, epinephrine and Mitomycin C. A syringe 100 is connected to a needle 101. The needle 101 is inserted under the conjunctiva 46 into the Tenon's capsule 47. The contents of the syringe 100 are injected into the Tenon's capsule 47 and massaged around the eye, which causes the Tenon's capsule 47 to hydrate and expand as is shown in FIG. 11.

Figure 13:
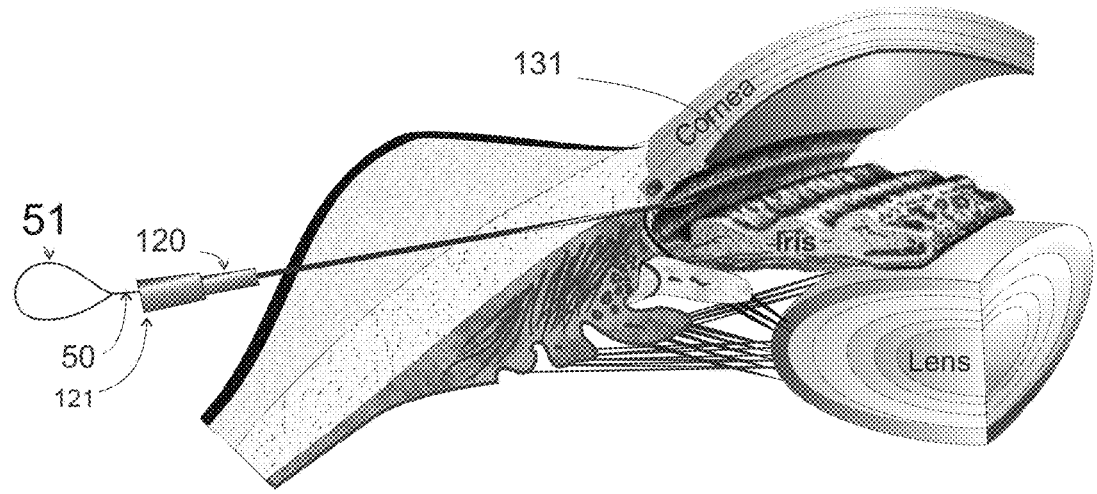
FIG. 13 is a view similar to FIG. 12 showing advancement of a guidewire through the needle and into the anterior chamber.

Looking now at FIG. 12, a hollow needle 120 is inserted through the conjunctiva 46, the Tenon's capsule 47, the sclera 48 to form a needle tract (first tissue passageway) that leads into the anterior chamber 42. The needle tract can bisect the angle between the cornea 41 and the iris 43 as shown. In FIG. 13, the guidewire 50 is inserted into the lumen of the needle 120 non-looped end first, such that a small portion 131 of the guidewire 50 extends out of a distal end of the needle 120 into the anterior chamber 42. FIG. 13 shows an open luer hub 121 at the proximal end of the needle 120. A syringe (e.g., syringe 100 of FIG. 10) or similarly a hemostasis valve or equivalent membrane can be attached to the luer hub 121 to prevent aqueous humor from leaking out of the open hub 121. Note that the guidewire 50 can be pre-inserted into the needle 120, before inserting the needle 120 into the eye, by a manufacturer to save loading time during the procedure. However, if the guidewire 50 is pre-inserted into the needle 120, the distal non-looped end of the guidewire 50 must be withdrawn into the needle 120, so that the non-looped end does not extend distally of the distal end of the needle 120 prior to insertion in the eye. Such withdrawal of the guidewire prior to insertion of the needle 120 prevents bending the guidewire which may damage ocular tissue.

Figure 14:
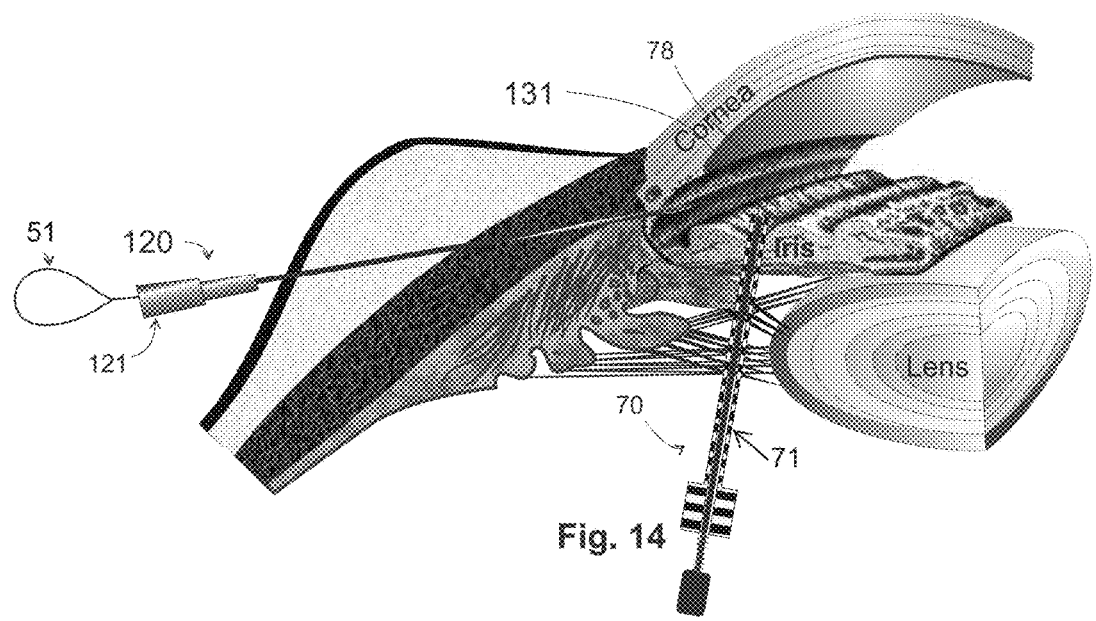
FIG. 14 is a view similar to FIG. 13 showing insertion of a snare through a corneal incision and extension of the snare over an end of the guidewire.
Figure 15:
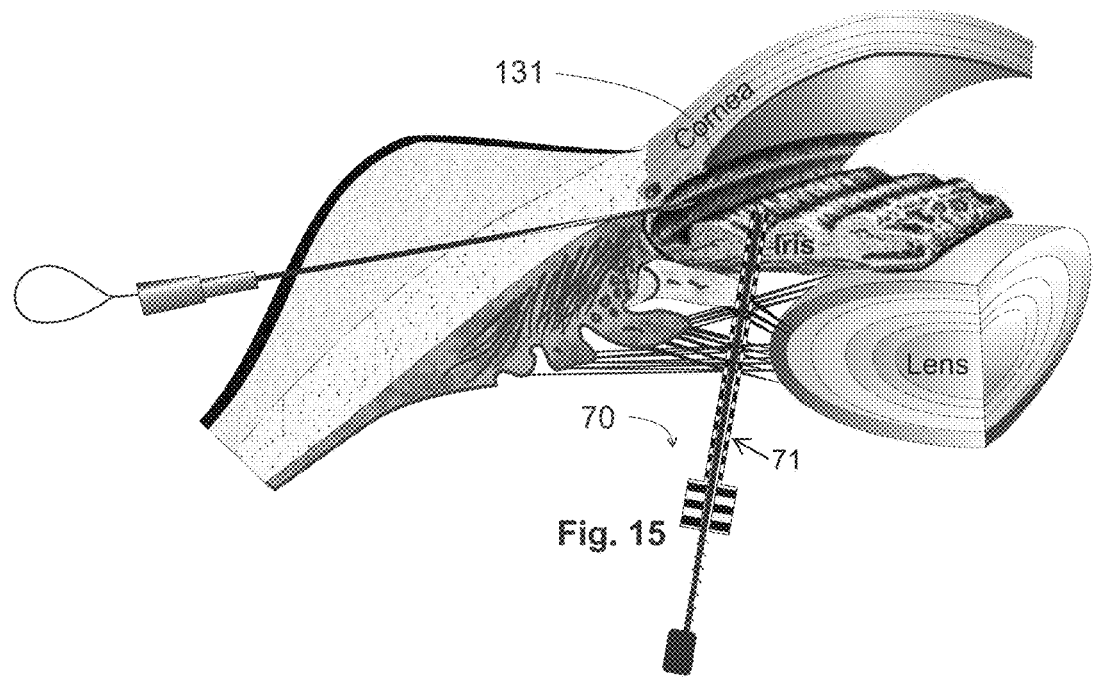
FIG. 15 is a view similar to FIG. 14 showing retraction of the snare and engagement of the end of the guidewire.

In FIG. 14, the snare 70, with its loop 78 in its closed or retracted configuration (FIG. 7B), is inserted through a corneal incision that forms a second tissue passageway leading into the anterior chamber 42 (not shown). The loop 78 is moved into its open or extended configuration (FIG. 7A) and around a portion of the guidewire segment 131. As shown in FIG. 15, according to one preferred aspect of the method, the loop 78 is retracted back into the outer sheath 71 of the snare 70, which causes the guidewire segment 131 to be folded onto itself and pulled into the outer sheath of the snare 70 and held firmly in place. Snare 70 can then be moved out of the eye by retracting the snare 70 back through the second tissue passageway (corneal incision), thereby pulling the guidewire 50 further into the needle 120. Retaining the folded guidewire segment 131 within the snare prevents the end of the guidewire from scratching the cornea 41.

The needle 120 is then removed from the needle tract (first tissue passageway) by retracting it proximally over the guidewire 50 and loop 51 leaving the guidewire 50 inside the needle tract as shown in FIG. 16. Note that loop 51 can be flexible and taper down in needle 120 during such retraction. The needle 120 can be discarded in a secure "sharps" container.

FIG. 17 shows the glaucoma drainage device 30 with a hook 171 attached to its distal end. Hook 171 is hooked into loop 51 of guidewire 50.

Figure 18:
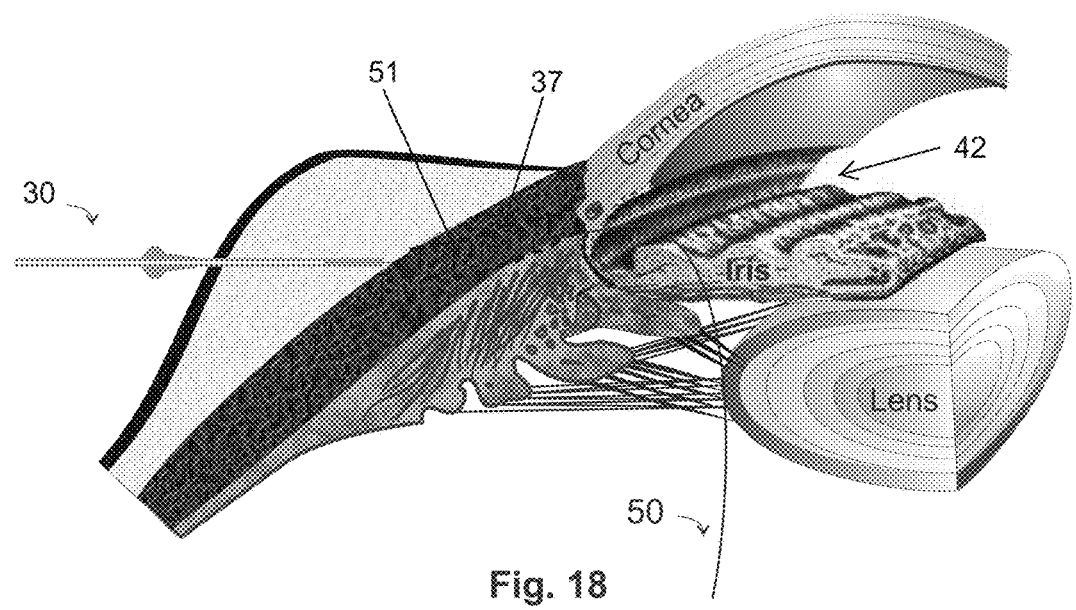
FIGS. 18 and 19 are views similar to FIG. 17, showing using the guidewire to pull the glaucoma drainage device into the needle tract and anterior chamber of the eye.
Figure 19:
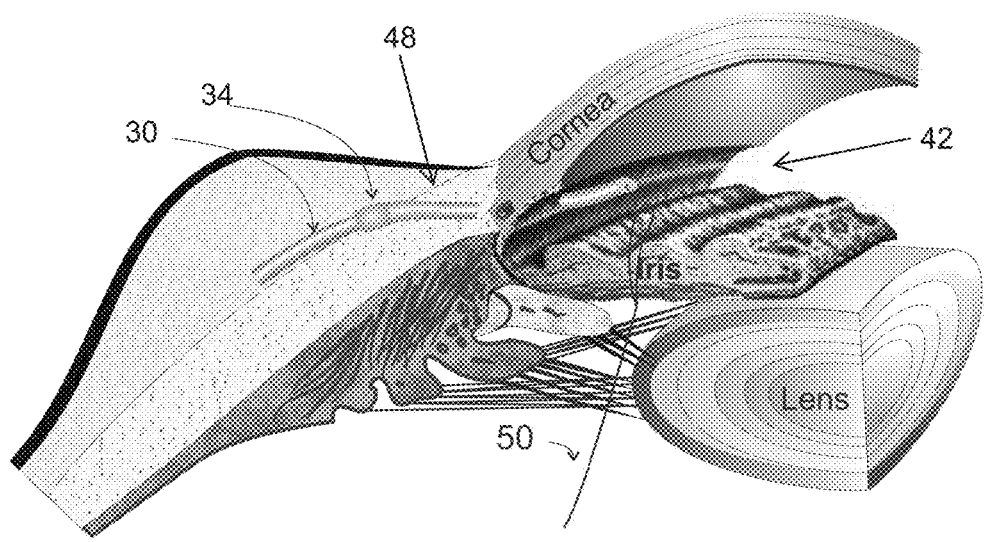

FIGS. 18 and 19 show glaucoma drainage device 30 being pulled into and though the needle tract (e.g., the needle tract 37 of FIG. 4B) by simply pulling the guidewire 50 out of the clear corneal incision (second tissue passageway). The glaucoma drainage device 30 is pulled to the point where the distant end of the glaucoma drainage device 30 is located inside the anterior chamber of the eye, the taper 35 is wedged into the sclera 48 to seal therewith, and the shoulder 34 remains outside the sclera 48 with its bearing surface 36 near to or bearing against the sclera 48 as shown in FIG. 19. The shoulder 34 may also seal with the sclera 48 if the taper 35 is pulled fully into sclera 48 or if the sclera 48 retracts proximally in contact with the shoulder 34.

Figure 20:
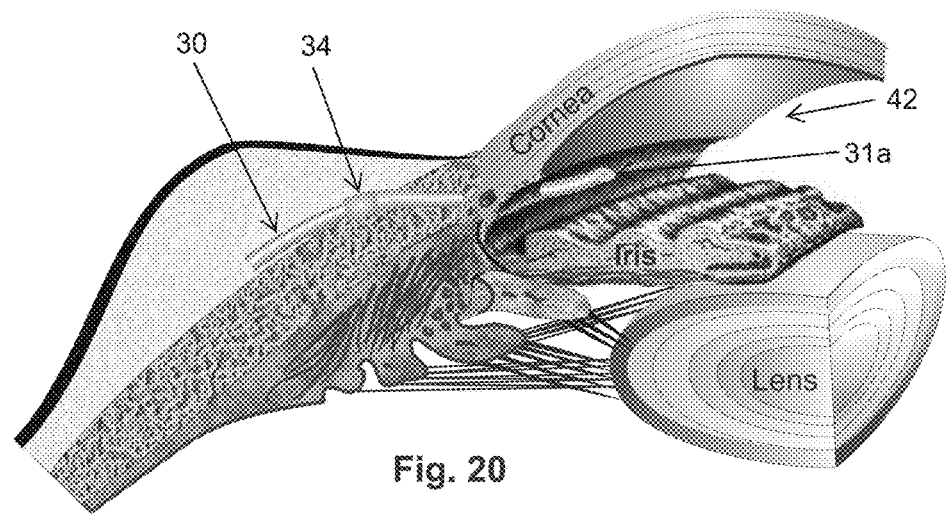
FIG. 20 illustrates the glaucoma drainage device in the implanted position in the eye.

The distal end 31a of glaucoma drainage device 30 can be made sufficiently long such that a portion of it can be pulled out of the cornea 41 before the shoulder 34 is positioned in its final implanted position. Once the shoulder 34 is situated near or against the sclera 48, the distal end 31a of glaucoma drainage device 30 can be pulled and stretched to an extent that the distal end 31a extends through the corneal incision (second tissue passageway) such that it can be severed or otherwise decoupled from the hook 171. The free distal end 31a can then retract back into the anterior chamber 42 so that the distal end 31a extends 1 mm to 3 mm into the anterior chamber 42. A mark (not shown) can be placed on the glaucoma drainage device 30, such as on the outer surface 31c, which can serve as a guide for severing (cutting) the glaucoma drainage device 30. Alternatively, a scissors can be inserted into a second clear corneal incision and the distal portion of the glaucoma device 30 can be trimmed (cut) to length when situated in the anterior chamber 42. Again, a mark (not shown) can be placed on the glaucoma drainage device 30 which can serve as a guide for trimming (cutting) the glaucoma drainage device 30. FIG. 20 shows the glaucoma drainage device 30 trimmed and in its final implanted position.

Figure 21:
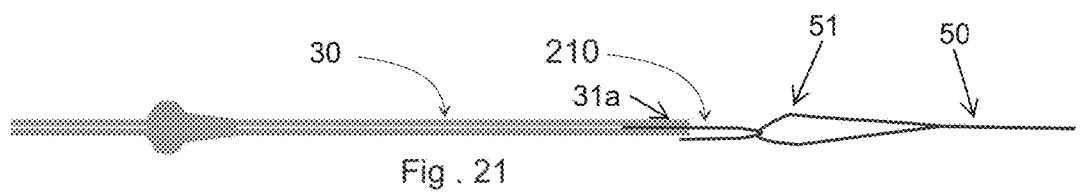
FIGS. 21 to 24 illustrate various structure and methods for temporarily securing an end of the glaucoma drainage device to the guidewire.
Figure 22:
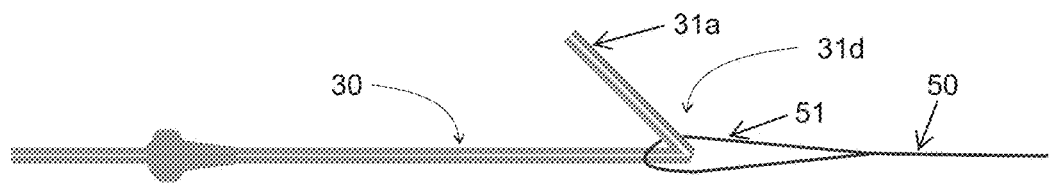
Figure 23:
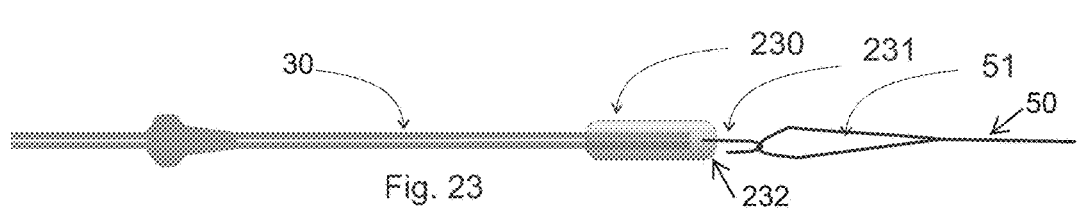
Figure 24:
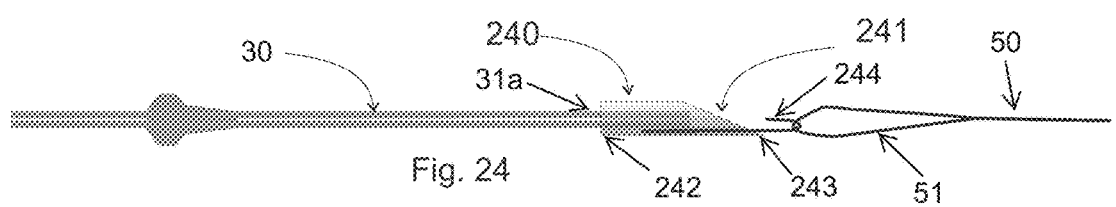

FIGS. 21 to 24 show different structures for and methods of securing the distal end 31a of the glaucoma drainage device 30 to the loop 51 of the guidewire 50 or loop 61 of the guidewire 60, according to various aspects of systems and methods of the disclosure. FIG. 21 shows a wire 210 protruding from glaucoma drainage device 30. The wire 210 is secured in place with an adhesive (such as cyanoacrylate or epoxy or UV curable cyanoacrylate). FIG. 21 also shows the wire 210 is formed as a hook and is connected to the loop 51 of guidewire 50. FIG. 22 shows the glaucoma drainage device 30 having its distal end 31a doubled over and coupled to loop 51 of guidewire 50. A reinforcing wire (not shown) may be placed in the angle 31d where the glaucoma drainage device 30 doubles over. Such a reinforcing wire may prevent the loop 51 of the guidewire 50 from inadvertently severing the glaucoma drainage device 30. FIG. 23 shows a small hollow cylinder 230 made from metal glued to the distal end 31a of the glaucoma device 30. A distal end 232 of the hollow cylinder 230 is soldered to a hooked wire 231. The hooked wire 231 is hooked to loop 51 of the guidewire 50. FIG. 24 shows a similar small hollow cylinder 240 made from a plastic such as polyimide or polysulfone glued on a first end 242 of the cylinder 240 to the distal end 31a of the glaucoma drainage device 30 and with a hooked wire 244 glued to a second end 243 of the cylinder 240. The cylinder 240 is beveled 241 on the second end to facilitate being pulled through the conjunctiva 46, Tenon's capsule 47, sclera 48, and cornea 41. FIG. 24 shows the hooked wire 244 coupled to the loop 51 of the guidewire 50.

Figure 25:
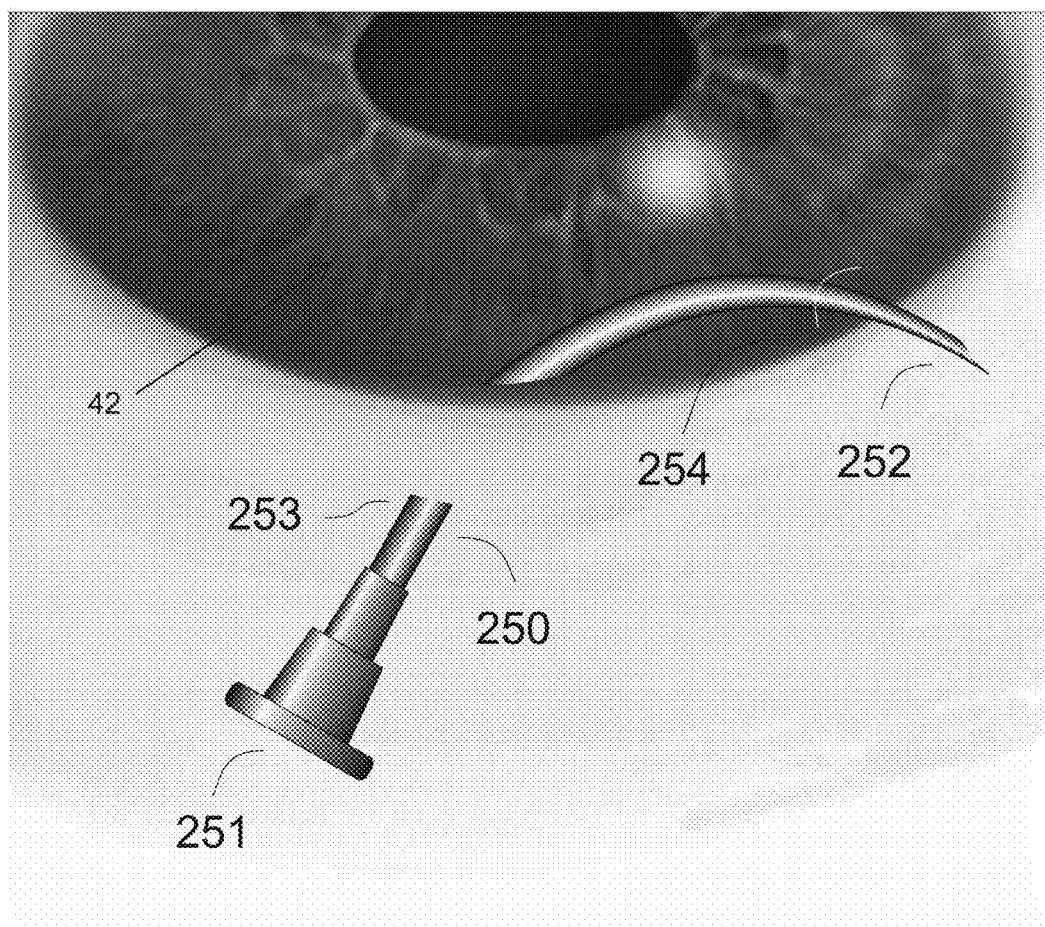
FIG. 25 illustrates an alternative method according for providing a needle into a cornea, through an anterior chamber, and out of the cornea for positioning a glaucoma drainage device.

FIG. 25 shows another method of implanting glaucoma drainage device 30. In this embodiment, a bent hollow needle 250 is provided with hub 251 and tip 252. The hollow need is first inserted in the conjunctiva 46 at entrance site 253 and maneuvered such that it forms a first tissue tract (first tissue passageway) leading into the anterior chamber 42, at which point the tip 252 is directed towards the cornea 41 to form a second tissue tract (first tissue passageway) that pierces the cornea 41 at exit site 254. Alternatively, the second tissue tract can intercept a corneal incision already made in the cornea 41 during the cataract surgery procedure. Once the needle 250 is in place, with the tip 252 sticking out of the cornea 41 (as shown in FIG. 25), guidewire 50 or 60 can be threaded through the needle 250 such that the loop 51 or 61 of the guidewire 50 or 60 extends from the hub 251 of the needle and the opposite end of the guidewire extends from the tip 252 of the needle 250. The needle 250 can then be removed by retracting the needle 250 over the guidewire so that the respective loops 51 and 61 remain outside the entrance site 253 of the first tissue tract. Any of the glaucoma device configurations shown in FIGS. 21 to 24 and FIG. 27, described below, can be connected to the loop 51 or 61 of the guidewire and pulled through the first tissue tract into place. Note that when using the configuration shown in FIG. 25, there is no need to use a snare or hooked rod.

Figure 26:
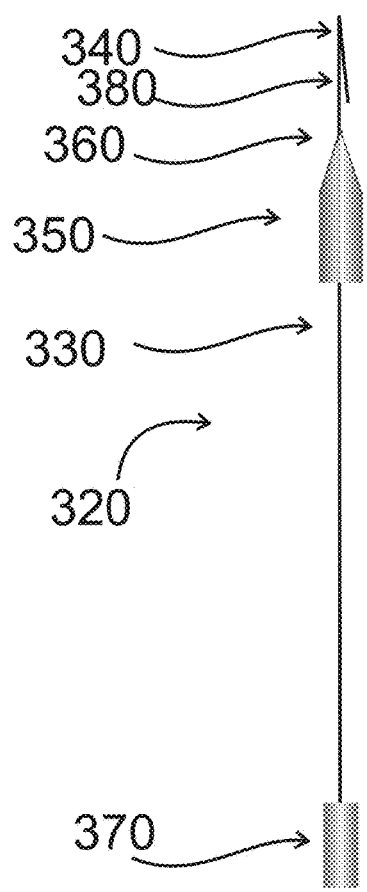
FIG. 26 shows a glaucoma drainage device carrier skeleton in accordance with the present disclosure.
Figure 27:
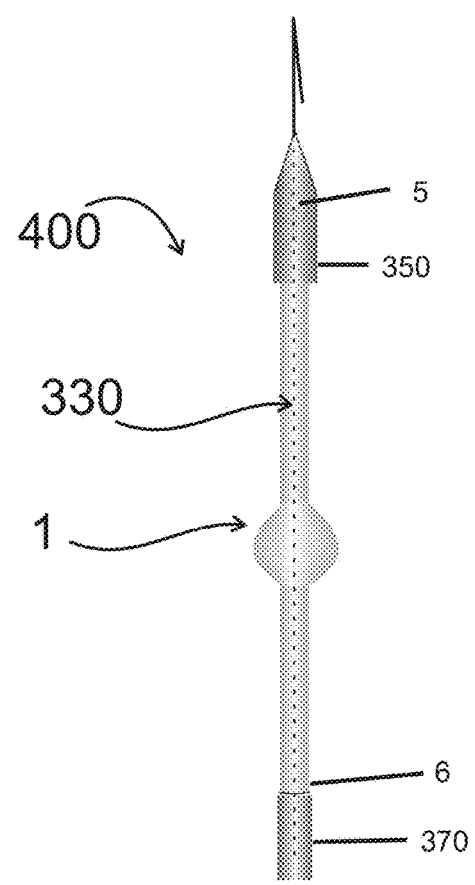
FIG. 27 shows a glaucoma drainage device carrier assembly in accordance with the present disclosure.

FIG. 26 shows a carrier 320 that may be used to capture and carry glaucoma drainage device 1 of FIG. 1 as shown in FIG. 27 such that the glaucoma drainage device 1 can be inserted into the eye 40 and positioned in a manner similar to that shown in FIGS. 4A and 4B. The carrier 320 includes a guidewire 330 and a hollow cap 350 and a retainer member 370 secured to the guidewire. The carrier 320 also includes a connector 340, which can be a hook or ball or the like, and shown in this example as a hook 340 on a distal end 380 of the guidewire 330. The hollow cap 350 is secured to the guidewire 330 at point 360. The hollow cap 350 can be made from stainless steel or somewhat rigid polymers such as polycarbonate, polyurethane, polyimide, polyester, polytetrafluoroethylene, polypropylene, polysulfone, and the like. As shown in FIG. 26, the hollow cap 350 has a tapered or conical distal tip. The guidewire 330 extends proximally from the hook 340 through the cap 350 to the retainer member 370, which is secured to the guidewire 330. The retainer member 370 may be detached from the guidewire 330 by severing the guidewire 330 just distally of retainer member 370 with a scissors, snips, and the like. Alternatively, the retainer member 370 can include a spring-loaded grasping mechanism (not shown) that can be configured to selectively grasp the guidewire 330 or be released therefrom.

The interior space of the hollow cap 350 can be configured to receive and carry one end (e.g., the distal tip 5) of the glaucoma drainage device 1, as shown in FIG. 27. In this configuration, the one end of the elongate ocular implant 1 is disposed and carried within the interior space of the hollow cap 350 without the one end of the glaucoma drainage device 1 being affixed to the hollow cap 350. The hollow cap 350 and the retaining member 370 are secured to the guidewire 330 at fixed positions offset from one another along the length of the guidewire 330 with the longitudinal spacing between the cap 350 and 370 fixed to accommodate the length of the glaucoma drainage device 1 and to prohibit the glaucoma drainage device from sliding out of the interior space of the opposed cap 350 during use. In this configuration, the retaining member 370 can be disposed adjacent to or near the other end (e.g., proximal end 6) of the glaucoma device 1. The guide wire 330, hollow cap 350, and retainer member 370 are configured to capture and carry the glaucoma drainage device 1 during deployment through ocular tissue.

FIG. 27 shows a carrier assembly 400 that includes the carrier 320 and the glaucoma drainage device 1. Specifically, the carrier assembly 400 is assembled with the guidewire 330 extending longitudinally through the elongated lumen 3 of the glaucoma drainage device 1 with the hollow cap 350 and the member 370 capturing the glaucoma device 1. In FIG. 27 the distal end 5 of the glaucoma drainage device 1 is disposed and carried within the interior space of the hollow cap 350 without being affixed to the hollow cap 350. Although FIGS. 26 and 27 show a relatively small hollow cap 350 just covering the tip 5 of the glaucoma drainage device 1, the hollow cap 350 can be longer and extend the full length of the distal end 5 of the glaucoma drainage device 1; that is, from the distal end 5 to the beginning of the fin 4. The guidewire 330 may have a diameter that is equal to or less than a diameter of the lumen 3 of the guidewire 330 to enable the guidewire 330 to easily be inserted and withdrawn from lumen 3. The glaucoma drainage device 1 is captured by the carrier 320, and the glaucoma device 1 can be removed from assembly 400 by cutting the wire 330 just above the detachable member 370 and pulling off the hollow cap 350 by the hook 340 with the remainder of the guidewire 330 assembly.

The guidewire 330 is configured to slide through the lumen of the glaucoma drainage device 1 such that the guidewire 330, hollow cap 350, and the retainer member 370 capture and carry the glaucoma drainage device 1 as the distal end 5 of the glaucoma drainage device 1 is pulled through the tissue tract 37 (FIG. 4B) such that the glaucoma drainage device 1 is implanted at the desired location, such as where the hollow cap 350 and the distal end 5 of the glaucoma drainage device 1 are positioned inside the anterior chamber 42 of the eye. The hollow cap 350 can be configured to enable moving and carrying the glaucoma drainage device 1 captured by the assembly 400 through ocular tissue without snagging the glaucoma drainage device 1 against such tissue, which might cause the tube 2 of the glaucoma drainage device to compress or buckle into an accordion. Also, the detachable retaining member 370 can prevent the guidewire 330 from inadvertently pulling out of glaucoma drainage device 1.

Note that the carrier 320 can also be used to capture and carry glaucoma drainage device 30 of FIG. 3 such that the glaucoma drainage device 30 can be inserted into the eye and positioned as shown in FIGS. 4A and 4B.

FIGS. 28A to 28G demonstrate a surgical method for implanting (deploying) the glaucoma drainage device 1 in the eye using the carrier assembly 340 of FIG. 27. Of course, the method is also applicable to implanting the glaucoma drainage device 30 when the glaucoma drainage device 30 is substituted for glaucoma device 1 in the carrier assembly 400. Regardless of which glaucoma drainage device is implanted, prior to the method shown in FIGS. 28A to 28G, it may be necessary to inject various drugs such as epinephrine, lidocaine, antibiotics, etc. under the conjunctiva 46 and Tenon's Capsule 47. Also, prior to or subsequent to implantation of the glaucoma device 1, it may be necessary to inject an antiproliferative drug such as Mitomycin C or 5-fluorouracil under the conjunctiva 46 and Tenon's Capsule 47. It may be preferable to inject the aforementioned drugs prior to implanting the glaucoma device 1 so as to loosen up the conjunctiva 46. It is also noteworthy that as a consequence of injecting the aforementioned drugs under the conjunctiva 25, the Tenon's Capsule 47 becomes hydrated. The hydrated Tenon's Capsule 47 forms a pocket or bleb 49 under the conjunctiva 46. The hydrated Tenon's Capsule 47 may at times be referred to as hydrodissected conjunctiva 46 or Tenon's Capsule 47. The pocket or bleb 49 thus formed can be massaged or milked such that the gathered tissue is accumulated close to the limbus 59. In this manner, if a needle is inserted through the conjunctiva 46 and the sclera 48 into the anterior chamber 42 through or below the accumulated tissue, when the conjunctiva 46 is returned to its normal resting place (e.g., shown in FIG. 4A), the hole through the conjunctiva 46 will be located more posterior to the hole in the sclera 48.

As part of the method, needle 120 can be used to form the needle tract (first tissue passageway) through the conjunctiva/Tenons through the sclera 48 and under the limbus 59 that leads into the anterior chamber 42 of the eye similar to that shown in FIG. 4B. The path of the needle 120 is such that when it enters the anterior chamber 42 it bisects an angle between the cornea 41 and the iris 43. In an area near the entrance site "I" where the needle 120 is inserted, the conjunctiva 46 may be scrunched up or milked anteriorly to enable penetration of the conjunctiva/Tenons through a thicker section to allow for better healing as well as to locate the conjunctiva wound in an area remote from the proximal end 6 of the glaucoma drainage device 1.

Figure 28A:
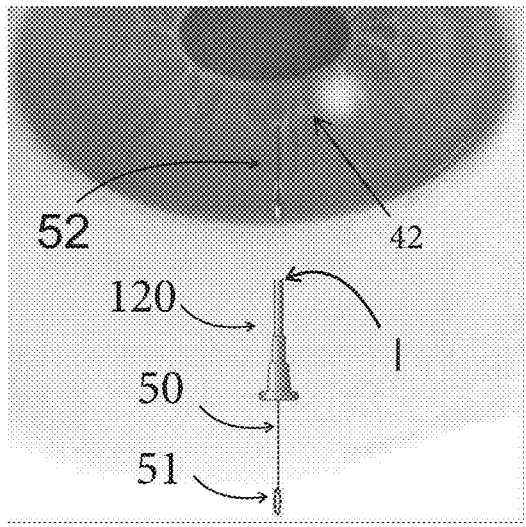
FIGS. 28A to 28G shows progressive steps of implanting the glaucoma drainage device of FIG. 1 with the glaucoma drainage device carrier assembly of FIG. 27.

With the tip of the needle 120 positioned in the anterior chamber 42, the distal end of the guidewire 50 can be slidably inserted through the lumen of the needle 120 and into the anterior chamber 42 of the eye 40 as shown in FIG. 28A. Also, guidewire 60 may be substituted for guidewire 50 in the workflow. The needle 120 can be 22 gauge to 27 gauge, and preferably is 25 gauge. In addition, the guidewire 50 and the needle hub can be contained in a syringe (not shown) or other fluid-stasis means (hemostasis valve, Tuohy Borst valve, etc.) to prevent aqueous humor from flowing through the needle lumen and deflating the eye.

Figure 28B:
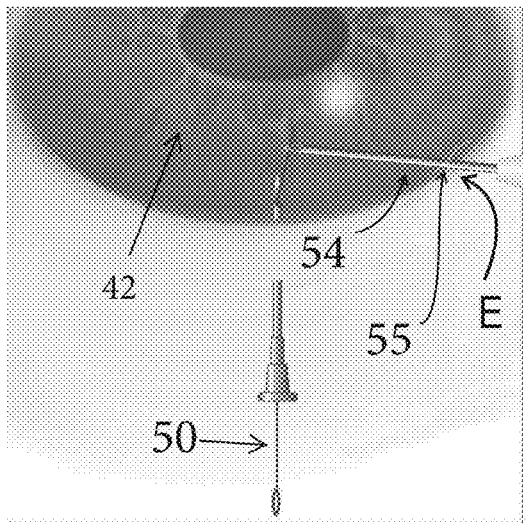
Figure 28C:
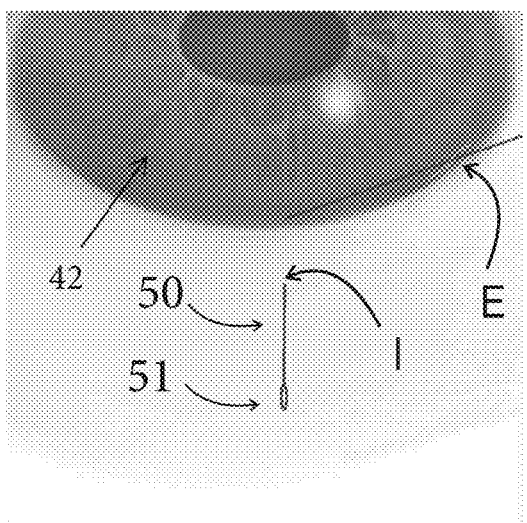

FIG. 28B shows a step of inserting a snare 54 through a clear corneal incision 55 (second tissue passageway) at site E that leads into the anterior chamber 42, and grabbing the distal end of the guidewire 50 with the snare 54. It will be appreciated that the snare 54 shown in FIG. 28B may be snare 70 or hooked rod 90 described above. Also, the guidewire 50 can also be grabbed by any grabbing means such as a forceps, needle clamps, hooks, magnets, and the like. With the distal end of the guidewire 50 grabbed by the snare 54, the snare 54 can be retracted out of the corneal incision 55 at site E such that the distal end of the guidewire 50 extends from the anterior chamber 42 and out through the corneal incision 55 at site E as shown in FIG. 28C. The needle 120 can also be retracted over the guidewire 50 past the loop 51 such that the loop 51 rests on the exterior of the eye offset from the entrance site I as shown in FIG. 28C.

Figure 28D:
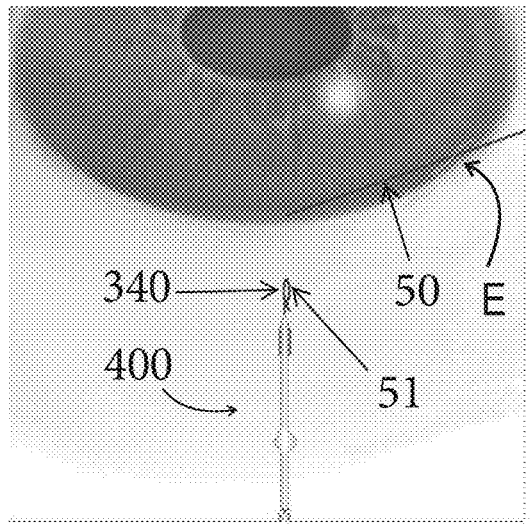

FIG. 28D shows a step of attaching the loop 51 of the guidewire 50 to the hook 340 of the carrier assembly 400.

Figure 28E:
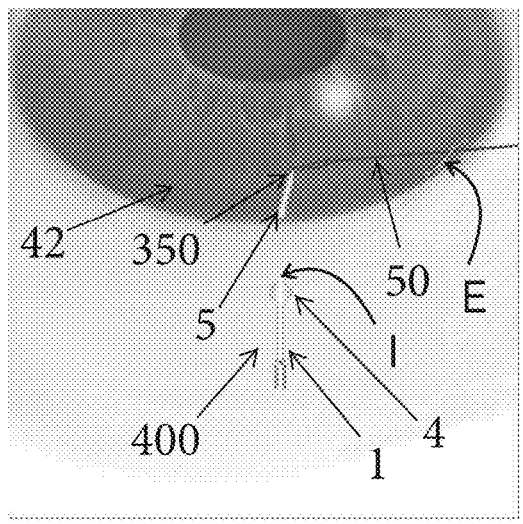

FIG. 28E shows a step of pulling the carrier assembly 400 through the needle tract formed by the needle 120 through the conjunctiva/Tenons under the limbus 59 and into the anterior chamber 42 of the eye 40. The carrier assembly 400 (particularly the distal portion of the device 1 captured by the guidewire 50 and the cap 350) can be pulled (moved) through this tissue tract by pulling the distal end of the guidewire 50 until the distal tip 5 of the glaucoma drainage device 1 is positioned inside the anterior chamber 42 of the eye. This position can be guided by positioning the fin 4 of the glaucoma drainage device 1 butted up against a proximal end of the needle tract formed by the needle 120. Then, the carrier assembly 400 can be pulled a little further into the needle tract with a slight force so that a short segment of the fin 4 is pulled into the needle tract to secure it in place and prevent peri-annular leakage.

Figure 28F:
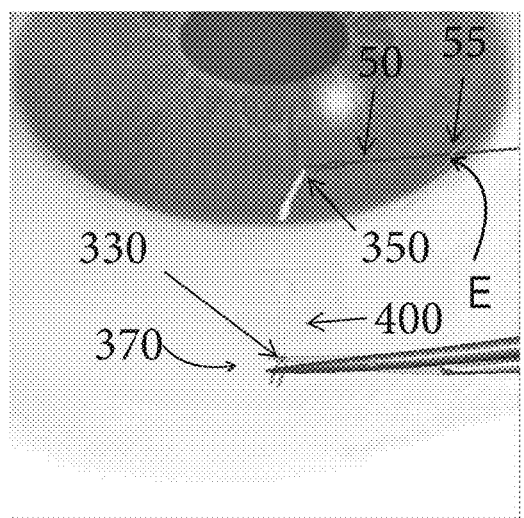

In a subsequent step shown in FIG. 28F, with the restraining member 370 and guidewire 330 exposed near the proximal end of the needle tract, scissors or other instrument can be used to cut or otherwise separate the restraining member 370 from the guidewire 330. Once the restraining member 370 is separated from the assembly 400, the free end of the guidewire 50 that extends out through the corneal incision 55 at site E can be pulled further, which effectuates pulling the cap 350 and guidewire 330 away from the distal end 5 of the glaucoma drainage device 1 and out through the corneal incision 55 at site E and thus leaving deployed in the eye the glaucoma drainage device 1 in its final position (such as the position shown in FIG. 4A).

Figure 28G:
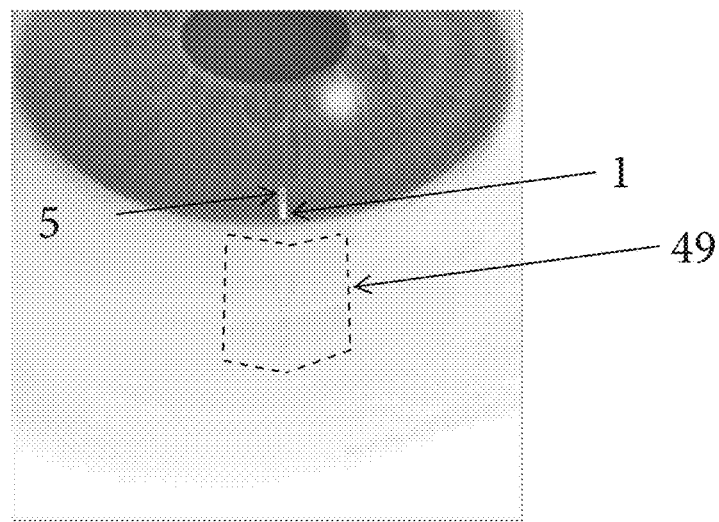

In a subsequent step shown in FIG. 28G, the conjunctiva 46 and Tenon's Capsule 47 may be unfurled to effectively bury the proximal end 6 of the glaucoma drainage device 1 into the pocket or bleb 49 formed under the conjunctiva 46 and Tenon's Capsule 47 as described above. The outline of the pocket or bleb 49 is shown as a dotted line in FIG. 28G. The glaucoma drainage device 1 can be tested for flow of aqueous humor and, if the flow is adequate, the remainder of the glaucoma drainage device 1 can be tucked under the Tenon's Capsule 47. The method can avoid the use of sutures to fixate the glaucoma drainage device 1 and to close the pocket or bleb into the glaucoma drainage device 1 drains. The hole in the conjunctiva 46 created by the needle 120 can be closed by any means generally used to close small holes in the conjunctiva 46; e.g., sutures, glue, cautery, or it can self-heal.

The methods described hereinabove describes how the glaucoma drainage devices 1 and 30 can be implanted through the conjunctiva 46 and Tenon's 47 and into the anterior chamber 42 without taking down the conjunctiva 46. It can be appreciated that these methods can also be used subsequent to taking down the conjunctiva 46. It can also be appreciated that the proximal end 6 of the glaucoma drainage device 1 or the proximal end 31b of the glaucoma drainage device 30 (the part not in the anterior chamber 42) can be located in the Tenon's 47 or under the Tenon's 47 or other locations in or around the eye.

There have been described and illustrated herein embodiments of a system for and method of implanting a glaucoma drainage device. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A method for treating glaucoma with an implantable glaucoma drainage device, the method comprising:
   inserting a hollow elongated needle into the eye to form a first tissue passageway leading to the anterior chamber of the eye;
   introducing a distal end of a guidewire through the needle and into the anterior chamber of the eye;
   introducing a snare through a second tissue passageway leading into the anterior chamber and using the snare to capture the distal end of the guidewire within the anterior chamber;
   moving the needle over the guidewire so as to remove the needle from the first tissue passageway without removing the guidewire from the first tissue passageway;
   coupling a glaucoma drainage device to a proximal end of the guidewire that extends outside a proximal end of the first tissue passageway; and
   using the snare to pull the captured guidewire segment and the glaucoma drainage device coupled thereto such that the glaucoma drainage device is pulled into the needle tract until the glaucoma drainage device is located in an implanted position in the eye.

2. The method according to claim 1, further comprising:
   removing the snare from the eye via the second tissue passageway.

3. The method according to claim 1, wherein:
   the snare has a sheath and a hook or loop inside the sheath and extendible therefrom; and
   the distal end of the guidewire is captured with the snare by i) surrounding the segment of the guidewire at a fold location of the segment with the loop or hook of the snare, ii) drawing the hook or loop into the sheath causing the segment of the guidewire to fold at the fold location, and iii) drawing the hook or loop further into the sheath to draw the folded segment of the guidewire into the sheath of the snare to protect the cornea from contact with the distal end of the guidewire.

4. The method according to claim 1, wherein:
   at least one of the proximal end and the distal end of the guidewire is formed as a loop.

5. The method according to claim 4, wherein:
   the guidewire is elastic and the loops open when removed from a compressed state upon removing the needle from over the guidewire.

6. The method according to claim 1, wherein:
   the guidewire has a diameter of 0.001 inches to 0.006 inches.

7. The method according to claim 1, wherein:
   the distal end of the guidewire is disposed inside the hollow needle when the hollow needle is inserted into the eye.

8. The method according to claim 1, wherein:
   the guidewire slides relative to an internal lumen of the hollow needle and in the first tissue passageway.

9. The method according to claim 8, wherein:
   the hollow needle has an inner diameter of 0.008 inches.

10. The method according to claim 1, further comprising:
    cutting a distal end of the glaucoma device.

11. The method according to claim 10, wherein:
    the cutting of the distal end of the glaucoma device is performed within the anterior chamber of the eye.

12. The method according to claim 11, further comprising:
    removing the cut distal end of the glaucoma device from the eye via the second tissue passageway.

* * * * *